United States Patent [19]

Pepe

[11] 4,209,455

[45] Jun. 24, 1980

[54] AMINOORGANOSILICON ACYLAMINO COMPOUNDS

[75] Inventor: Enrico J. Pepe, Amawalk, N.Y.

[73] Assignee: Union Carbide Corporation, New York, N.Y.

[21] Appl. No.: 974,615

[22] Filed: Dec. 29, 1978

[51] Int. Cl.$^2$ .............................................. C07F 7/18
[52] U.S. Cl. .................................. 556/419; 556/413; 556/418; 556/424
[58] Field of Search ........................... 260/448.8 R

[56] References Cited

U.S. PATENT DOCUMENTS

| | | | |
|---|---|---|---|
| 2,928,858 | 3/1960 | Morehouse | 260/448.8 R |
| 3,033,815 | 5/1962 | Pike et al. | 260/448.8 R X |
| 3,477,901 | 11/1969 | Keil | 260/448.8 R X |
| 3,671,562 | 6/1972 | Pepe et al. | 260/448.8 R |
| 3,700,844 | 10/1972 | Domba | 260/448.8 R X |
| 3,702,860 | 11/1972 | Krahnke | 260/448.8 R |
| 3,754,971 | 8/1973 | Pepe et al. | 260/31.2 R X |
| 3,900,679 | 8/1975 | Marzocchi | 260/448.8 R X |

*Primary Examiner*—Helen M. S. Sneed
*Attorney, Agent, or Firm*—Richard J. Gallagher

[57] ABSTRACT

Aminoorganosilicon compounds containing a single acylamino group and at least one secondary and/or tertiary amino group in the same substituent radical.

11 Claims, No Drawings

AMINOORGANOSILICON ACYLAMINO COMPOUNDS

BACKGROUND OF THE INVENTION

This invention relates to novel aminoorganosilicon acylamino compounds.

Silicon containing polyazimide compounds are well known in the art as seen by U.S. Pat. No. 3,746,738. However, such compounds contain at least two acylamino groups and at least one secondary and/or tertiary amino group in the same substituent radical. The novel silicon compounds of this invention are distinguished from such polyazimide compounds in that they contain only a single acylamino group and at least one secondary and/or tertiary amino groups in the same substituent radical.

SUMMARY OF THE INVENTION

Thus it is an object of this invention to provide novel aminoorganosilicon acylamino compounds. Other objects and advantages of this invention will become readily apparent from the following description and appended claims.

More specifically, this invention may be described as relating to novel aminoorganosilicon acylamino compounds having the formula

wherein:

X is an alkoxy radical having 1 to 6 carbon atoms; R is a divalent alkylene radical having 1 to 4 carbon atoms; $R^1$ is hydrogen or an alkyl radical having 1 to 4 carbon atoms; $R^2$ is a divalent alkylene radical having 2 to 4 carbon atoms; $R^3$ is a radical selected from the group consisting of hydrogen, an alkyl radical having 1 to 20 carbon atoms or a phenyl radical; $R^4$ is a radical selected from the group consisting of an alkyl radical having 1 to 20 carbon atoms, a phenyl radical or a silyl radical of the formula:

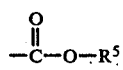

wherein X, R and $R^1$ are the same as defined above; Q is a radical selected from the group consisting of hydrogen, an alkyl radical of 1 to 4 carbon atoms, a phenyl radical or an ester radical of the formula —COOR$^5$ wherein $R^5$ is an alkyl radical having 1 to 4 carbon atoms; and wherein a has a value of 0 to 2 and t and x each have a value of 0 to 4, with the proviso that when x is at least 1, $R^4$ can also be hydrogen.

DESCRIPTION OF THE PREFERRED EMBODIMENTS

Illustrative radicals represented by X above include alkoxy radicals having 1 to 6 carbon atoms, such as methoxy, ethoxy, propoxy, 2-methoxyethoxy, isopropoxy, hexyloxy and the like, the preferred alkoxy radicals being methoxy, ethoxy and 2-methoxyethoxy. Illustrative divalent alkylene radicals represented by R above include methylene, ethylene, propylene, isopropylene, butylene and the like, the preferred divalent alkylene groups being ethylene (—C$_2$H$_4$—) and propylene (—C$_3$H$_6$—). Illustrative radicals represented by $R^1$ above include alkyl radicals such as methyl, ethyl, propyl, isopropyl, butyl and the like. Illustrative divalent alkylene radicals represented by $R^2$ above include ethylene, propylene, isopropylene, butylene, and the like, the preferred divalent alkylene groups being ethylene and propylene. Illustrative radicals represented by $R^3$ above include hydrogen, phenyl and alkyl radicals having from 1 to 20 carbon atoms such as methyl, ethyl, propyl, octyl, octadecyl, eicosyl and the like. Preferably $R^3$ is hydrogen. Illustrative radicals represented by $R^4$ above include hydrogen, phenyl, alkyl radicals having from 1 to 20 carbon atoms such as methyl, ethyl, propyl, octyl, octadecyl, eicosyl, and the like as well as silyl groups of the formula

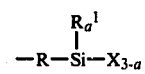

wherein R, $R^1$, X and a are the same as defined above. Preferably $R^4$ represents a silyl group. Illustrative radicals represented by Q above include hydrogen, phenyl, alkyl radicals having from 1 to 4 carbon atoms such as methyl, ethyl, propyl, butyl and the like, as well as ester radicals of the formula

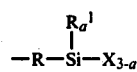

wherein $R^5$ represents an alkyl radical having from 1 to 4 carbon atoms such as methyl, ethyl, propyl, butyl, and the like. Preferably Q is hydrogen. In the more preferred aminoorganosilicon acylamino compounds of this invention a is preferably O. Of course, it is understood that each individual radical or group represented by the above symbols may be the same or different in any given compound.

The aminoorganosilicon acylamino compounds of this invention can be prepared by following simple processing procedures involving the use of Michael addition products as the starting materials. For example, aminosilane compounds of the formula

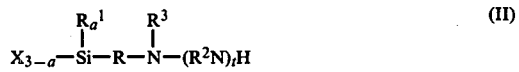

wherein X, R, $R^1$, $R^2$, $R^3$, a and t are the same as defined above can be reacted with an olefinic carboxylate ester by the Michael addition method to form the corresponding amino-carboxylic acid ester of the silane and carboxylate materials employed as seen by the following illustration:

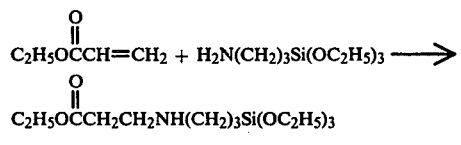

Intermediate I

The amino-carboxylic acid ester-silane intermediate product so formed can then be subsequently amidated with either (1) a primary amino silicon compound of Formula (II) above, (2) a primary organoamine, or (3) a primary organic polyamine to produce the desired aminoorganosilicon acylamino compounds of this invention depicted by Formula (I) above as seen by the following illustrations

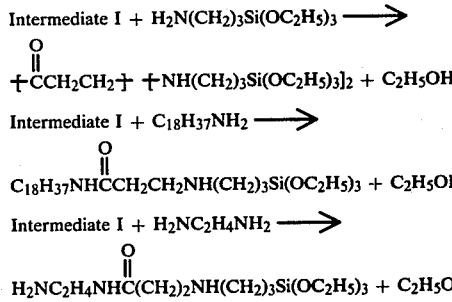

The amino-carboxylic acid ester containing silane compounds employable as the starting materials for such types of processes as depicted above and/or the Michael addition method for their preparation are well known in the art as seen for example by U.S. Pat. No. 2,929,829 and may be illustrated by the following formula

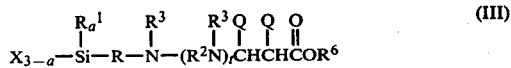 (III)

wherein R, R$^1$, R$^2$, R$^3$, Q, X, a and t are the same as defined above and R$^6$ is a monovalent hydrocarbon radical, preferably an alkyl radical having 1 to 4 carbon atoms such as methyl, ethyl, propyl, butyl, and the like.

Illustrative examples of olefinic carboxylate compounds which may be employed in such a Michael addition process include those of the formula

 (IV)

wherein Q and R$^6$ are the same as defined above such as,
CH$_2$=CHCOOC$_2$H$_5$
CH$_2$=CHCOOCH$_3$
CH$_2$=C(CH$_3$)COOCH$_3$
CH$_3$CH=CHCOOC$_2$H$_5$
C$_6$H$_5$CH=CHCOOC$_2$H$_5$
CH$_3$OOCCH=CHCOOCH$_3$
and the like.

Illustrative aminosilanes that can be employed in such a Michael addition process include those of Formula (II) above such as
(CH$_3$O)$_3$SiCH$_2$NH$_2$
(C$_2$H$_5$O)$_3$Si(CH$_2$)$_3$NH$_2$
(CH$_3$O)$_3$Si(CH$_2$)$_3$NH$_2$
(CH$_3$O)$_3$Si(CH$_2$)$_3$NHCH$_3$
(C$_3$H$_7$O)$_3$Si(CH$_2$)$_3$NH$_2$
(CH$_3$OC$_2$H$_4$O)$_3$Si(CH$_2$)$_3$NH$_2$
(C$_2$H$_5$O)$_2$CH$_3$Si(CH$_2$)$_3$NH$_2$
(C$_2$H$_5$O)$_2$C$_2$H$_5$Si(CH$_2$)$_3$NH$_2$
(C$_2$H$_5$O)$_3$Si(CH$_2$)$_2$NH$_2$
(C$_2$H$_5$O)$_3$SiCH$_2$CH$_2$CH(CH$_3$)NH$_2$
(C$_2$H$_5$O)$_3$Si(CH$_2$)$_4$NH$_2$
(CH$_3$O)$_3$Si(CH$_2$)$_3$NH(CH$_2$)$_2$NH$_2$
(C$_4$H$_9$O)$_2$(CH$_3$)Si(CH$_2$)$_3$NHCH$_3$
(CH$_3$O)$_3$Si(CH$_2$)$_3$(NHC$_2$H$_4$)$_2$NH$_2$
(CH$_3$O)$_3$Si(CH$_2$)$_3$(NHC$_2$H$_4$)$_3$NH$_2$
(C$_2$H$_5$O)$_3$Si(CH$_2$)$_3$(NHC$_2$H$_4$)$_4$NH$_2$
(C$_2$H$_5$O)$_2$CH$_3$Si(CH$_2$)$_4$NH$_2$
(CH$_3$O)(CH$_3$)$_2$Si(CH$_2$)$_4$NH$_2$
(CH$_3$O)$_3$Si(CH$_2$)$_3$NHC$_4$H$_9$
(C$_2$H$_5$O)$_3$Si(CH$_2$)$_3$NHCH$_3$
(C$_2$H$_5$O)$_3$SiCH$_2$CH(CH$_3$)NH$_2$
and the like.

The processing conditions of said Michael addition are well known and taught e.g. in U.S. Pat. No. 2,929,829 and in this instance, merely involve forming a mixture of about 1 mole of the aminosilicon compound and about one mole of the olefinic carboxylate compound and maintaining the mixture at a temperature, preferably about room temperature, until the aminosilicon compound has added to the double bond of the olefinic carboxate thereby producing the desired Michael addition product.

As pointed out above the aminoorganosilicon acylamino compounds of this invention as shown by Formula (I) above can be produced by amidating an aminocarboxylic acid ester containing silane of Formula (III) above with either (1) a primary aminosilane compound of Formula (II) above; (2) a primary organic amine or (3) a primary organic polyamine.

Illustrative primary aminosilane reactants include those of the formula

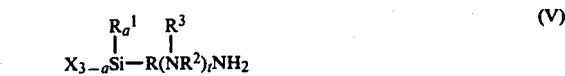 (V)

wherein R, R$^1$, R$^2$, R$^3$, X, a and t are the same as defined above such as
(CH$_3$O)$_3$SiCH$_2$NH$_2$
(C$_2$H$_5$O)$_3$Si(CH$_2$)$_3$NH$_2$
(CH$_3$O)$_3$Si(CH$_2$)$_3$NH$_2$
(CH$_3$O)$_3$Si(CH$_2$)$_4$NH$_2$
(C$_3$H$_7$O)$_3$Si(CH$_2$)$_3$NH$_2$
(CH$_3$OC$_2$H$_4$O)$_3$Si(CH$_2$)$_3$NH$_2$
(C$_2$H$_5$O)$_2$CH$_3$Si(CH$_2$)$_3$NH$_2$
(C$_2$H$_5$O)$_2$C$_2$H$_5$Si(CH$_2$)$_3$NH$_2$
(C$_2$H$_5$O)$_3$SiCH$_2$CH$_2$CH(CH$_3$)NH$_2$
(C$_2$H$_5$O)$_3$Si(CH$_2$)$_4$NH$_2$
(CH$_3$O)$_3$Si(CH$_2$)$_3$NH(CH$_2$)$_2$NH$_2$
(CH$_3$O)$_3$Si(CH$_2$)$_3$(NHC$_2$H$_4$)$_2$NH$_2$
(CH$_3$O)$_3$Si(CH$_2$)$_3$(NHC$_2$H$_4$)$_3$NH$_2$
(C$_2$H$_5$O)$_3$Si(CH$_2$)$_3$(NHC$_2$H$_4$)$_4$NH$_2$
(C$_2$H$_5$O)$_2$(CH$_3$)Si(CH$_2$)$_4$NH$_2$
(CH$_3$O)(CH$_3$)$_2$Si(CH$_2$)$_4$NH$_2$
(C$_2$H$_5$O)$_3$SiCH$_2$CH(CH$_3$)NH$_2$
and the like.

Illustrative primary organic amines includes those of the formula

R$^7$NH$_2$ (VI)

wherein R$^7$ is a monovalent hydrocarbon radical having from 1 to 20 carbon atoms, such as methylamine, ethylamine, propylamine, octylamine, octadecylamine, eicosylamine, phenylamine, and the like.

Illustrative primary organic polyamines include those of the formula

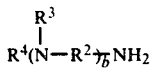
(VII)

wherein $R^2$, $R^3$, $R^4$ and $R^4$ are the same as defined above, and b has a value of 1 to 4, such as $H_2NCH_2CH_2NH_2$
$H\text{-}[NHCH_2CH_2]_2NH_2$
$H\text{-}[NHCH_2CH_2]_3NH_2$
$H\text{-}[NHCH_2CH_2]_4NH_2$
$H_2NCH_2CH_2CH_2NH_2$
$H\text{-}[NHCH_2CH_2CH_2]_2NH_2$
$H(CH_3)NCH_2CH_2NH_2$
$H(C_2H_5)NCH_2CH_2NH_2$
$H(C_4H_9)NCH_2CH_2CH_2NH_2$
$H(C_6H_5)NCH_2CH_2NH_2$
$(CH_3)_2NCH_2CH_2NH_2$
$(C_2H_5)_2NCH_2CH_2NH_2$
$H_2NCH_2CH_2NHCH_2CH_2CH_2NH_2$ and the like.

Of course, it is obvious that the particular choice of amidation processes will merely depend upon which type of silane product is desired and that all three of the above depicted amidation processes can be carried out merely by forming a mixture of a carboalkoxyalkylaminoorganosilane such as shown in Formula (III) above with any of the amino compounds shown in Formulas (V), (VI) or (VII) above and maintaining the mixture at a temperature at which the carboalkoxy group and primary amino group react to produce the desired aminoorganosilicon/acylamino compound.

The relative amounts of the two reactants used as the starting materials for said above amidation processes is not narrowly critical. For example, from one to ten chemical equivalents of primary amine starting materials of Formulas (V), (VI) or (VII) can be employed for each mole of the carboalkoxyalkylaminosilane of Formula III above. However, an excess of such primary amine reactants is not desirable unless the unreacted excess can be readily removed from the reaction mixture or does not interfere with the intended use of the desired silane condensation product. In general, however, when the amino starting material is an aminosilane of Formula (V) above or a primary amine of Formula (VI) above or a primary polyamine of Formula (VII) above that contains only one primary amino group it is preferred that the carboalkoxyalkylaminoorganosilane starting material be reacted with a stoichiometric amount (1 mole to 1 mole) of said amino starting materials. On the other hand, when the amino starting material is a primary polyamine of Formula (VII) above that contains two primary amino groups it is essential to employ a stoichiometric excess of said polyamine in order to avoid producing bis-silylated compounds containing more than a single acylamino group. Moreover, while it is preferred to prepare the aminoorganosilicon acylamino compounds of this invention by first forming the amino carboxylic acid ester containing silane intermediate of Formula (III) above and then reacting said intermediate with the primary amino starting material it is to be understood that, if desired the bis silylated compounds of this invention can also be prepared in a single step for example, by reacting an olefinic compound of Formula (IV) above that contains only one carboalkoxy group with a primary aminosilane of Formula (V) above using a mole ratio of 0.5 moles of the carboxylate compound to 1 mole of the aminosilane. It is generally preferred to employ an olefinic carboxylate starting material which contains the same type of alkoxy group as the alkoxy radicals of the aminosilane starting material since when different alkoxy groups are involved (e.g. in the reaction of methyl acrylate and a triethoxy containing silane starting material) the process can lead to a mixed methoxy-ethoxy silane adduct intermediate and/or an acylamino containing mixed methoxy-ethoxy silane product.

The above amidation processes may be carried out over a wide range of temperatures such as from 0° C. to 200° C.; however, it is generally preferred to employ a temperature in the range of from about 25° C. to about 150° C. The by-product alcohol may be removed by any conventional method such as by distillation and pressures other than atmospheric pressure may be used to aid in the removal of the alcohol if desired. Of course, it is to be understood that the aminoorganosilicon acylamino compounds of this invention can be employed in their crude product form or purified if desired after removal of the alcohol by any conventional method such as further distillation. Moreover, it is often desirable to employ a catalyst to accelerate the condensation reaction (amidation) between the carboalkoxy group and primary amino group of the starting materials. Illustrative catalysts which may be employed for this purpose are the tin catalysts described in U.S. Pat. No. 2,890,208 as well as other metal catalysts such as those described in U.S. Pat. No. 3,169,945.

Accordingly, illustrative aminoorganosilicon acylamino compounds of this invention include such compounds as

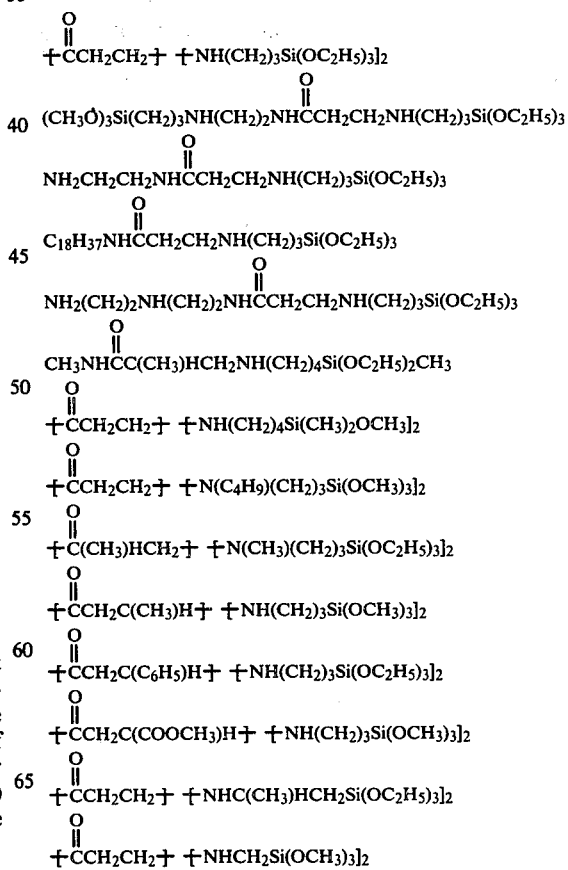

-continued

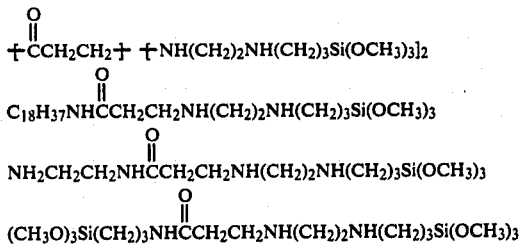

and the like. The most preferred aminoorganosilicon compounds of this invention are the bis-silyl compounds, especially

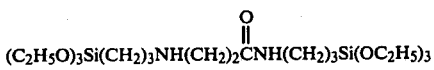

The aminoorganosilicon acylamino compounds of this invention have a wide range of utility and may be employed in the same manner as conventionally known amino containing silanes. For example, they can be hydrolyzed and condensed with or without other conventional organosilanes to form polymericsiloxanes such as those containing the structural unit

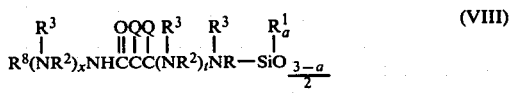 (VIII)

wherein R, $R^1$, $R^2$, $R^3$, Q, a t and x are the same as defined above $R^8$ is a radical selected from the group consisting of an alkyl radical having 1 to 20 carbon atoms, a phenyl radical or a siloxy radical of the formula

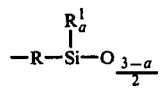

wherein R, $R^1$ and a are the same as defined above, with the proviso that when x is at least one $R^4$ can also be hydrogen; as well as copolymers and terpolymers containing at least one siloxy unit of Formula VIII above and at least one siloxy unit of the formula

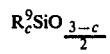

wherein $R^9$ represents a substituted or unsubstituted monovalent hydrocarbon radical and c has a value of 0 to 2, e.g. a dimethylsiloxy unit. Of course, it is to be understood that such polymeric materials may be linear, branched or cyclic, and can be endblocked in any conventional manner desired, such as by siloxy units of the formula

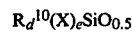

wherein X is a hydrolyzable group, $R^{10}$ is substituted or unsubstituted monovalent hydrocarbon radical such as alkyl or aryl, d has a value of 0 to 3 and e has a value of 0 to 3, the sum of d+e being 3. The aforedescribed aminoorganosilicon acylamino compounds of this invention as well as the above described polymeric siloxanes may be used as sizes for fibrous materials, particularly fibrous glass materials in the same manner as heretofore conventional silicon coupling agents have been employed in combination with a broad variety of thermosetting and/or thermoplastic resins such as disclosed in U.S. Pat. No. 3,754,971. Said silanes and siloxanes may also be used as coupling agents for other inorganic substances such as siliceous pigments and fillers, e.g. clay, silica, hydrated silica, fumed silica, sand and the like. In addition the organooaminosilicon acylamino compounds of this invention are particularly useful additives for hydroxyl containing organic thermoplastic polymer compositions that result in room temperature curable coatings that provide protective and solvent resistant cured coatings for a wide variety of substrates such as metals, plastics, wood, cloth, foam, glass, and the like, as disclosed in assignee's concurrently filed U.S. application Ser. No. 974,614, entitled "Ambient Temperature Curable Hydroxyl Containing Polymer/Silicon Compositions".

The following examples illustrate the present invention and are not to be regarded as limitative. All parts and percentages are by weight unless otherwise specified.

EXAMPLE 1

About 276.3 grams (1.25 moles) of gamma-aminopropyltriethoxysilane was added to a 500 ml., 3 necked flask equipped with a mechanical stirrer, heating mantle, addition funnel, thermometer and distillation head and receiver protected by a nitrogen by-pass. About 53.8 grams (0.62 moles) of methyl acrylate was then rapidly added via a funnel with stirring and cooling at such a rate that the contents of the flask were maintained below 25° C. After addition, the contents of the flask were stirred for about 3 hours at room temperature and then about 0.66 grams (0.2 weight percent) of dibutyl tin oxide added as catalyst and the reaction mixture heated to about 135° C. to 150° C. with the appearance of refluxing alcohol (methanol and ethanol) in the distillation head. About 16.2 grams (theory 19.8 grams, assuming all the distillate to be methanol) of said alcohol mixture was removed and collected over 2.5 hours to yield about 307.7 grams (theory 310 grams) of the crude mixed methoxyethoxy silane reaction product.

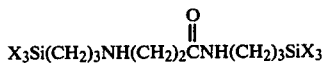

wherein each X is individually selected from the class consisting of methoxy and ethoxy radicals. An amine analysis of said silane product showed 2.01 moles N/kg. (theory 2.02 moles titratable N/kg.). Gas chromatographic analysis of the elutable materials of said silane product showed it to consist of about 11.39 weight percent of alcohol (methanol and ethanol), about 7.25 weight percent of mixed methoxy-ethoxy silane $X_3Si(CH_2)_3NH_2$ wherein X is the same as defined above, about 6.27 weight percent of the mixed methoxy-ethoxy silane Michael adduct intermediate $X_3Si(CH_2)_3NHCH_2CH_2COOCH_3$ wherein X is the same as defined above, and about 71.43 weight percent of the acylamino containing mixed methoxy-ethoxy silane

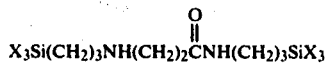

wherein X is the same as defined above, while the remainder of said product did not elute.

EXAMPLE 2

About 1105 grams (5.0 moles) of gamma-aminopropyltriethoxysilane was added to a 2 liter, 3 necked flask having the same experimental set-up as described in Example 1. Then while stirring about 250.3 grams (2.5 moles) of ethyl acrylate was rapidly added to the flask over 15 minutes while maintaining the temperature below 25° C. After the heat of reaction has subsided, about 2.71 grams (0.2 weight percent) of dibutyl tin oxide catalyst was added and the reaction mixture heated to 145° C. to 150° C. for five hours after which about 86.3 grams (theory 115.0 grams) of ethanol was distilled off under vacuum to yield about 1247.4 grams (theory 1240.0 grams) of the crude silane reaction product

An amine analysis of said silane product showed 2.18 moles N/kg. (theory 2.02 moles titratable N/kg.). Gas chromatographic analysis of the elutable materials of said silane product showed it to consist of about 10.1 weight percent ethanol, about 8.0 weight percent of gamma-aminopropyltriethoxysilane, about 5.2 weight percent of the Michael addition intermediate (C$_2$H$_5$O)$_3$-Si(CH$_2$)$_3$NH(CH$_2$)$_2$COOC$_2$H$_5$, and about 73.3 weight percent of the acylamino containing triethoxysilane

while the remainder of the product did not elute. Nuclear magnetic resonance analysis of the crude silane reaction product confirmed the above silane product structure.

EXAMPLE 3

About 895 grams (5.0 moles of gamma-aminopropyltrimethoxysilane and about 215.2 grams (2.5 moles) of methyl acrylate were allowed to react, while stirring at room temperature, in a two liter, 3 necked flask having the same experimental set-up as described in Example 1. After the methyl acrylate was consumed, the reaction mixture was heated to 135° C. at 100–160 mmHg. over 4 hours and about 27.3 grams of methanol collected. The reaction mixture was cooled to room temperature and about 2.22 grams (0.2 weight percent) of dibutyl tin oxide catalyst added. The reaction mixture was then reheated to 135° C. at 80 mmHg. for two hours and an additional 62.9 grams of methanol collected (total methanol collected=90.2 grams, theory 80 grams) to yield about 1017.7 grams (theory 1030 grams) of the crude silane reaction product

An amine analysis of said silane product showed 2.7 moles N/kg. (theory 2.42 moles titratable N/kg.). Gas chromatographic analysis of the elutable materials of said silane product showed 13.5 weight percent methanol, 11.0 weight percent of gamma-aminopropyltrimethoxysilane, about 16.0 weight percent of the Michael addition intermediate (CH$_3$O)$_3$Si(CH$_2$)$_3$NH(CH$_2$)$_2$COOCH$_3$ and about 54.5 weight percent of the acylamino containing trimethoxysilane

while the remainder of the product did not elute.

EXAMPLE 4

Following the same procedure as described in Example 1, about 151.9 grams (0.68 moles) of (CH$_3$O)$_3$-Si(CH$_2$)$_3$NH(CH$_2$)$_2$NH$_2$ with an amine analysis of 8.82 moles N/kg. (theory 9.0 moles N/kg) distilled from commercial grade N-beta-(aminoethyl)-gamma-aminopropyltrimethoxysilane was allowed to react while stirring and cooling to maintain the temperature at about room temperature with about 28.4 grams (0.33 moles) of methyl acrylate. After one hour amine analysis of the reaction mixture was about 7.27 moles N/kg. (theory 6.49 moles titratable N/kg.). Nuclear magnetic resonance analysis indicated total disappearance of acrylate protons, but the retention of the carboxymethoxy methyl group protons while the concentration of —NH-protons and the remainder of the spectrum was consistent with the Michael addition adduct structure.

The reaction mixture was then heated to 150° C. for 4 hours, distilling 6.0 grams of methanol. A nuclear magnetic resonance analysis at this point of the experiment indicated greater than 90% methanol formation (or less than 10% carbomethoxy methyl group remaining). The distillation was completed under vacuum producing an additional 6.2 grams of methanol (total methanol 12.2 grams, theory 10.6 grams) and yielding about 159.7 grams (theory 164.3 grams) of the crude silane reaction product

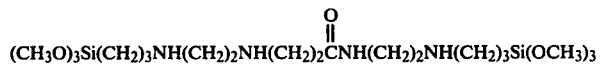

An amine analysis of said silane product showed 5.89 moles N/kg. (theory 6.02 moles titratable N/kg.). Gas chromatographic analysis of the elutable materials of said silane product showed about 1.0 weight percent methanol, about 9.9 weight percent (CH$_3$O)$_3$-Si(CH$_2$)$_3$NH(CH$_2$)$_2$NH$_2$, about 4.6 weight percent of the Michael addition intermediate (CH$_3$O)$_3$-Si(CH$_2$)$_3$NH(CH$_2$)$_2$NH(CH$_2$)$_2$COOCH$_3$ while the remainder of said crude silane product did not elute. Nuclear magnetic resonance analysis of the crude silane reaction product confirmed the above silane product structure.

Example 5

A 500 ml., 3 neck flask having the same experimental set-up as described in Example 1 was charged with about 168.9 grams (0.53 moles) of $(C_2H_5O)_3Si(CH_2)_3NH(CH_2)_2COOC_2H_5$, about 160.7 grams (0.53 moles) of octadecyl amine (88.9% pure by amine titration) and about 0.824 grams (0.25 weight percent) of dibutyl tin oxide catalyst and the stirred reaction mixture heated to a final temperature of about 160° C. over a period of about 16 hours while removing 24.7 grams (0.53 moles) of 98.3% pure ethyl alcohol to produce the amber, wax-like crude silane product

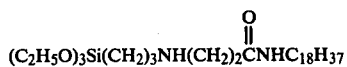

$$(C_2H_5O)_3Si(CH_2)_3NH(CH_2)_2\overset{O}{\underset{\|}{C}}NHC_{18}H_{37}$$

An amine analysis of said silane product made by dissolving a 1 gram aliquot of the product in 25 ml. of warm acetic acid (75%)/ethanol (25%) and titrating potentiometrically with a standardized solution of percholoric acid dissolved in acetic acid showed 1.64 meg./gm. of amino group versus 1.74 meg./gm. theoretical for the pure silane product. Infrared absorption characteristics of said silane product confirmed the above silane product structure.

Example 6

Following the procedures described herein above various Michael adduct intermediate products may be prepared such as shown by TABLE I below, which intermediates may then be reacted as described herein to produce various illustrative aminoorganosilicon acylamino compounds of this invention as seen by TABLE II below.

TABLE I
PRODUCTION OF CARBOALKOXYALKYLAMINOORGANOSILANE INTERMEDIATES

| Ex. No. | Olefinic Carboxylate | Aminoorganosilane | Michael Adduct Intermediate | Intermediate No. |
|---|---|---|---|---|
| 1 | $CH_2=CHCOOC_2H_5$ | $NH_2(CH_2)_3Si(OC_2H_5)_3$ | $C_2H_5OOC(CH_2)_2NH(CH_2)_3Si(OC_2H_5)_3$ | I |
| 2 | $CH_2=CHCOOCH_3$ | $NH_2(CH_2)_3Si(OC_2H_5)_3$ | $CH_3OOC(CH_2)_2NH(CH_2)_3Si(OC_2H_5)_3$ | II |
| 3 | $CH_2=C(CH_3)COOC_2H_5$ | $NH_2(CH_2)_4Si(OC_2H_5)_2CH_3$ | $C_2H_5OOCC(CH_3)HCH_2NH(CH_2)_4Si(OC_2H_5)_2CH_3$ | III |
| 4 | $CH_2=CHCOOCH_3$ | $NH_2(CH_2)_4Si(CH_3)_2OCH_3$ | $CH_3OOC(CH_2)_2NH(CH_2)_4Si(CH_3)_2OCH_3$ | IV |
| 5 | $CH_2=CHCOOCH_3$ | $C_4H_9NH(CH_2)_3Si(OCH_3)_3$ | $CH_3OOC(CH_2)_2N(C_4H_9)(CH_2)_3Si(OCH_3)_3$ | V |
| 6 | $CH_2=C(CH_3)COOC_2H_5$ | $CH_3NH(CH_2)_3Si(OC_2H_5)_3$ | $C_2H_5OOCC(CH_3)HCH_2N(CH_3)(CH_2)_3Si(OC_2H_5)_3$ | VI |
| 7 | $CH_3CH=CHCOOCH_3$ | $NH_2(CH_2)_3Si(OCH_3)_3$ | $CH_3OOCCH_2C(CH_3)HNH(CH_2)_3Si(OCH_3)_3$ | VII |
| 8 | $C_6H_5CH=CHCOOC_2H_5$ | $NH_2(CH_2)_3Si(OC_2H_5)_3$ | $C_2H_5OOCCH_2C(C_6H_5)HNH(CH_2)_3Si(OC_2H_5)_3$ | VIII |
| 9 | $CH_3OOCCH=CHCOOCH_3$ | $NH_2(CH_2)_3Si(OCH_3)_3$ | $CH_3OOCCH_2C(COOCH_3)HNH(CH_2)_3Si(OCH_3)_3$ | IX |
| 10 | $CH_2=CHCOOC_2H_5$ | $NH_2C(CH_3)HCH_2Si(OC_2H_5)_3$ | $C_2H_5OOC(CH_2)_2NHC(CH_3)HCH_2Si(OC_2H_5)_3$ | X |
| 11 | $CH_2=CHCOOCH_3$ | $NH_2CH_2Si(OCH_3)_3$ | $CH_3OOC(CH_2)_2NHCH_2Si(OCH_3)_3$ | XI |
| 12 | $CH_2=CHCOOCH_3$ | $NH_2CH_2CH_2NH(CH_2)_3Si(OCH_3)_3$ | $CH_3OOC(CH_2)_2NH(CH_2)_2NH(CH_2)_3Si(OCH_3)_3$ | XII |
| 13 | $CH_2=CHCOOC_2H_5$ | $NHCH_2CH_2NH(CH_2)_3Si(OC_2H_5)_3$ | $C_2H_5O\overset{O}{\underset{\|}{C}}(CH_2)_2NH(CH_2)_2NH(CH_2)_3Si(OC_2H_5)_3$ | XIII |

TABLE II
PRODUCTION OF AMINOALKYLSILICON SILICON ACYLAMINE COMPOUNDS

| Michael Adduct Intermediate No. | Primary Amine | Acylamino Condensation Product | Ex. No. |
|---|---|---|---|
| I | $NH_2(CH_2)_3Si(OC_2H_5)_3$ | $\{\overset{O}{\underset{\|}{C}}CH_2CH_2\}\{NH(CH_2)_3Si(OC_2H_5)_3\}_2$ | 1 |
| I | $NH_2(CH_2)_2NH(CH_2)_3Si(OCH_3)_3$ | $(CH_3O)_3Si(CH_2)_3NH(CH_2)_2NH\overset{O}{\underset{\|}{C}}CH_2CH_2NH(CH_2)_3Si(OC_2H_5)_3$ | 2 |
| I | $NH_2CH_2CH_2NH_2$ | $NH_2CH_2CH_2NH\overset{O}{\underset{\|}{C}}CH_2CH_2NH(CH_2)_3Si(OC_2H_5)_3$ | 3 |
| I | $C_{18}H_{37}NH_2$ | $C_{18}H_{37}NH\overset{O}{\underset{\|}{C}}CH_2CH_2NH(CH_2)_3Si(OC_2H_5)_3$ | 4 |
| II | $NH_2(CH_2)_2NH(CH_2)_2NH_2$ | $NH_2(CH_2)_2NH(CH_2)_2NH\overset{O}{\underset{\|}{C}}CH_2CH_2NH(CH_2)_3Si(OC_2H_5)_3$ | 5 |
| III | $CH_3NH_2$ | $CH_3NH\overset{O}{\underset{\|}{C}}C(CH_3)HCH_2NH(CH_2)_4Si(OC_2H_5)_2CH_3$ | 6 |
| IV | $NH_2(CH_2)_4Si(CH_3)_2OCH_3$ | $\{\overset{O}{\underset{\|}{C}}CH_2CH_2\}\{NH(CH_2)_4Si(CH_3)_2OCH_3\}_2$ | 7 |
| V | $C_4H_9NH(CH_2)_3Si(OCH_3)_3$ | $\{\overset{O}{\underset{\|}{C}}CH_2CH_2\}\{N(C_4H_9)(CH_2)_3Si(OCH_3)_3\}_2$ | 8 |
| VI | $CH_3NH(CH_2)_3Si(OC_2H_5)_3$ | $\{\overset{O}{\underset{\|}{C}}C(CH_3)HCH_2\}\{N(CH_3)(CH_2)_3Si(OC_2H_5)_3\}_2$ | 9 |
| VII | $NH_2(CH_2)_3Si(OCH_3)_3$ | $\{\overset{O}{\underset{\|}{C}}CH_2C(CH_3)H\}\{NH(CH_2)_3Si(OCH_3)_3\}_2$ | 10 |

TABLE II-continued
PRODUCTION OF AMINOALKYLSILICON SILICON ACYLAMINE COMPOUNDS

| Michael Adduct Intermediate No. | Primary Amine | Acylamino Condensation Product | Ex. No. |
|---|---|---|---|
| VIII | $NH_2(CH_2)_3Si(OC_2H_5)_3$ | $[CCH_2C(C_6H_5)H]$ $[NH(CH_2)_3Si(OC_2H_5)_3]_2$ with C=O | 11 |
| IX | $NH_2(CH_2)_3Si(OCH_3)_3$ | $[CCH_2C(COOCH_3)H]$ $[NH(CH_2)_3Si(OCH_3)_3]_2$ with C=O | 12 |
| X | $NH_2C(CH_3)HCH_2Si(OC_2H_5)_3$ | $[CCH_2CH_2]$ $[NHC(CH_3)HCH_2Si(OC_2H_5)_3]_2$ with C=O | 13 |
| XI | $NH_2CH_2Si(OCH_3)_3$ | $[CCH_2CH_2]$ $[NHCH_2Si(OCH_3)_3]_2$ with C=O | 14 |
| XII | $NH_2(CH_2)_2NH(CH_2)_3SiO(CH_3)_3$ | $[CCH_2CH_2]$ $[NH(CH_2)_2NH(CH_2)_3Si(OCH_3)_3]_2$ with C=O | 15 |
| XII | $C_{18}H_{37}NH_2$ | $C_{18}H_{37}NHC(CH_2)_2NH(CH_2)_2NH(CH_2)_3Si(OCH_3)_3$ with C=O | 16 |
| XII | $NH_2CH_2CH_2NH_2$ | $NH_2CH_2CH_2NHCCH_2CH_2NH(CH_2)_2NH(CH_2)_3Si(OCH_3)_3$ with C=O | 17 |
| XII | $NH_2(CH_2)_3Si(OCH_3)_3$ | $(CH_3O)_3Si(CH_2)_3NHC(CH_2)_2NH(CH_2)_2NH(CH_2)_3Si(OCH_3)_3$ with C=O | 18 |
| XIII | $NH_2(CH_2)_2NH(CH_2)_3Si(OC_2H_5)_3$ | $[CCH_2CH_2]$ $[NH(CH_2)_2NH(CH_2)_3Si(OC_2H_5)_3]_2$ with C=O | 19 |

Various modifications and variations of this invention will be obvious to a worker skilled in the art and it is to be understood that such modifications and variations are to be included within the purview of this application and the spirit and scope of the appended claims.

What is claimed is:

1. An aminoorganosilicon acylamino compound having the formula

wherein:

X is an alkoxy radical having 1 to 6 carbon atoms; R is a divalent alkylene radical having 1 to 4 carbon atoms; $R^1$ is hydrogen or an alkyl radical having 1 to 4 carbon atoms; $R^2$ is a divalent alkylene radical having 2 to 4 carbon atoms; $R^3$ is a radical selected from the group consisting of hydrogen, an alkyl radical having 1 to 20 carbon atoms or a phenyl radical; $R^4$ is a radical selected from the group consisting of an alkyl radical having 1 to 20 carbon atoms, a phenyl radical or a silyl radical of the formula:

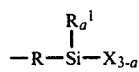

wherein X, R and Rhu 1 are the same as defined above; Q is a radical selected from the group consisting of hydrogen, an alkyl radical of 1 to 4 carbon atoms, a phenyl radical or an ester radical of the formula —$COOR^5$ wherein $R^5$ is an alkyl radical having 1 to 4 carbon atoms; and wherein a has a value of 0 to 2 and t and x each have a value of 0 to 4, with the proviso that when x is at least 1, $R^4$ can also be hydrogen.

2. A compound as defined in claim 1, wherein $R^3$ is hydrogen; Q is hydrogen; t is 0 or 1; x is 0 and $R^4$ is an alkyl radical.

3. A compound as defined in claim 1, wherein $R^3$ is hydrogen; Q is hydrogen; t is 0 or 1; x is 1 and $R^4$ is hydrogen or an alkyl radical.

4. A compound as defined in claim 1, wherein $R^3$ is hydrogen; Q is hydrogen; t is 0 or 1; x is 0 and $R^4$ is a silyl radical of the formula

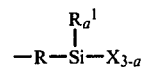

Wherein R, $R^1$ and X and a are the same as defined above.

5. A compound as defined in claim 4 wherein a is 0; t is 0; R is —$CH_2CH_2CH_2$—; and X is an alkoxy radical selected from the group consisting of methoxy, ethoxy and 2-methoxyethoxy radicals.

6. A compound as defined in claim 5, wherein X is a methoxy radical.

7. A compound as defined in claim 5, wherein X is an ethoxy radical.

8. A compound as defined in claim 1, wherein $R^3$ is hydrogen; Q is hydrogen; t is 0 or 1; x is 1 and $R^4$ is a silyl radical of the formula

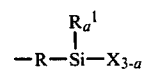

wherein R, $R^1$ and X and a are the same as defined above.

9. A compound as defined in claim 8, wherein a is 0; t is 1; R is —$CH_2CH_2CH_2$—; $R^2$ is —$CH_2CH_2$— and X is an alkoxy radical selected from the group consisting of methoxy, ethoxy and 2-methoxyethoxy radicals.

10. A compound as defined in claim 9, wherein X is a methoxy radical.

11. A compound as defined in claim 9, wherein X is an ethoxy radical.

* * * * *